United States Patent
Sharpe et al.

(10) Patent No.: US 10,379,029 B2
(45) Date of Patent: Aug. 13, 2019

(54) FLOW CELL

(71) Applicant: CYTONOME/ST, LLC, Boston, MA (US)

(72) Inventors: Johnathan Charles Sharpe, Hamilton (NZ); Rudolf Hulspas, Maynard, MA (US); Kristopher Scott Buchanan, Fort Collins, CO (US)

(73) Assignee: CYTONOME/ST, LLC, Bedford, MA (US)

( * ) Notice: Subject to any disclaimer, the term of this patent is extended or adjusted under 35 U.S.C. 154(b) by 830 days.

(21) Appl. No.: 14/030,946

(22) Filed: Sep. 18, 2013

(65) Prior Publication Data

US 2014/0170697 A1    Jun. 19, 2014

Related U.S. Application Data

(60) Provisional application No. 61/702,532, filed on Sep. 18, 2012.

(51) Int. Cl.
*G01N 33/00* (2006.01)
*G01N 15/14* (2006.01)
*G01F 13/00* (2006.01)

(52) U.S. Cl.
CPC ..... *G01N 15/1436* (2013.01); *G01N 15/1404* (2013.01); *G01N 15/1459* (2013.01); *G01N 2015/149* (2013.01); *Y10T 436/25375* (2015.01)

(58) Field of Classification Search
CPC ......... G01N 2015/149; G01N 15/1459; G01N 15/1436; G01N 15/1404; G01N 15/1434;
(Continued)

(56) References Cited

U.S. PATENT DOCUMENTS 5,293,219 A * 3/1994 Ayer ................. G01N 15/1404
                                                  356/335
6,079,836 A    6/2000 Burr et al.
(Continued)

FOREIGN PATENT DOCUMENTS

JP    2003-107099    10/1998
WO    98/45683 A1    10/1998
(Continued)

OTHER PUBLICATIONS

International Preliminary Report on Patentability for International Patent Application No. PCT/US2013/060454, dated Mar. 24, 2015.
(Continued)

*Primary Examiner* — Dean Kwak
(74) *Attorney, Agent, or Firm* — McCarter & English, LLP; David R. Burns

(57) ABSTRACT

A flow cell for particle processing such as particle sorting, may be operatively engaged to a particle processing apparatus. The fluid contact surfaces of the flow cell may be fully enclosed. Further, the flow cell may encapsulate all fluid contact surfaces in the particle processing apparatus. The enclosing or encapsulation of the fluid contact surfaces insures, improves or promotes operator isolation and/or product isolation. The flow cell may employ any suitable technique for processing particles. The flow cell may be disposable and suitable for use in droplet sorting. The flow cell may include an operatively sealed sort chamber having a particle stream focusing region, an orifice, an interrogation zone and a sorting region.

15 Claims, 12 Drawing Sheets

(58) Field of Classification Search
CPC ... G01N 2015/1452; G01N 2021/6469; G01N 21/49; G01N 15/147; G01N 2015/1438; G01N 2015/1497; G01N 15/1484; G01N 2015/1006; G01N 21/6428; B01L 2200/0652; B01L 2300/0816; B01L 2300/0864; B01L 3/502776; B01L 2200/0636; B01L 2200/0663; B01L 2300/0654
USPC .......................................... 422/73; 73/861.41
See application file for complete search history.

(56) References Cited

U.S. PATENT DOCUMENTS

| | | | |
|---|---|---|---|
| 6,281,018 | B1 | 8/2001 | Kirouac et al. |
| 7,118,048 | B2 | 10/2006 | Williams et al. |
| 8,246,805 | B2 | 8/2012 | Shinoda |
| 9,034,259 | B2* | 5/2015 | Kanda ................ G01N 15/14 422/50 |
| 2003/0138967 | A1* | 7/2003 | Hall .................... B01L 1/50 436/174 |
| 2005/0103690 | A1 | 5/2005 | Kawano et al. |
| 2006/0170912 | A1 | 8/2006 | Mueth et al. |
| 2009/0107893 | A1* | 4/2009 | Schembri .......... G01N 15/1459 209/127.1 |
| 2011/0271746 | A1 | 11/2011 | Shinoda et al. |
| 2012/0277902 | A1 | 11/2012 | Sharpe et al. |
| 2014/0004559 | A1 | 1/2014 | Hill et al. |
| 2014/0174206 | A1* | 6/2014 | Akiyama ............ B01L 3/0268 73/863 |
| 2015/0129688 | A1 | 5/2015 | Buchanan et al. |

FOREIGN PATENT DOCUMENTS

| | | |
|---|---|---|
| WO | 01/40765 A2 | 6/2001 |
| WO | 2010/056859 A1 | 5/2010 |
| WO | 2013/018273 | 2/2013 |

OTHER PUBLICATIONS

International Search Report and Written Opinion for International Patent Application No. PCT/US2013/060454, dated May 2, 2014.
Chen et al., "Micromachining Techniques for Fabrication of Micro and Nano Structures", INTECH deel 'Fundamentals of Laser Ablation of the Materials Used in Microfluidics', (Feb. 2012) pp. 35-60.
Schneider et al., "'Hydrophilic Coating Materials' Sol-Geltechnologies for Glass Producers and Users", (2004) pp. 187-194.

* cited by examiner

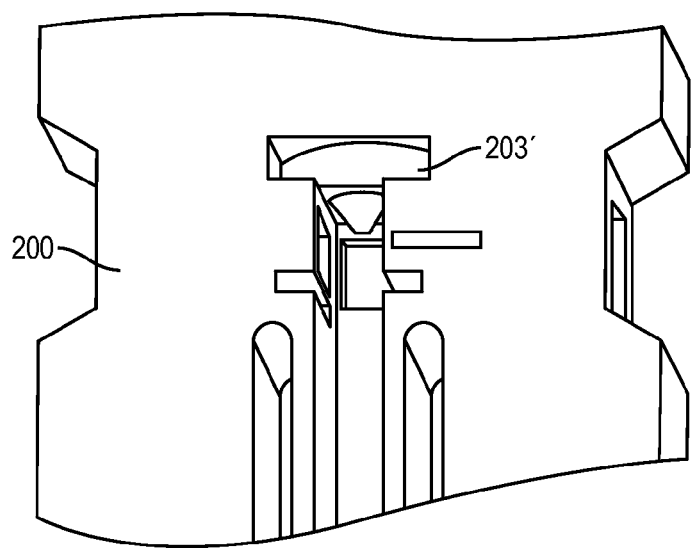
FIG. 10A
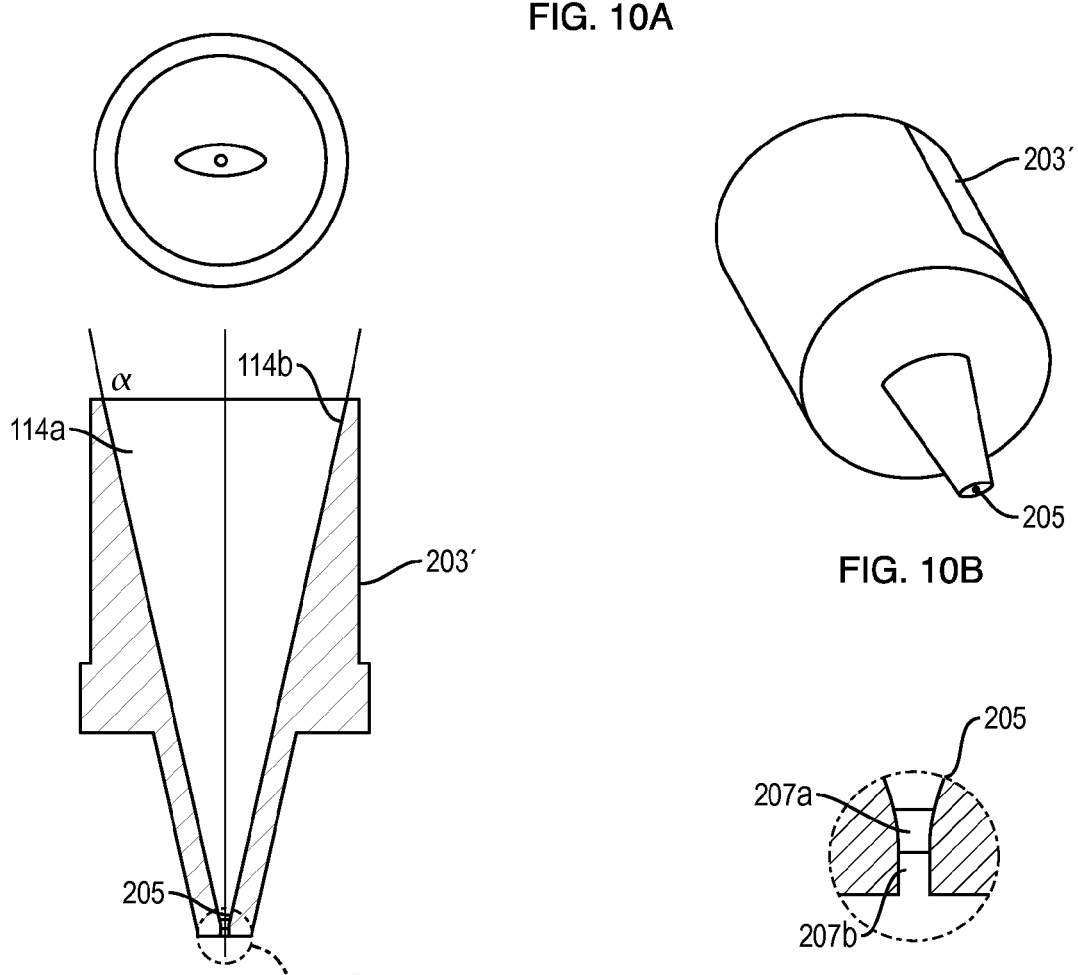
FIG. 10B
FIG. 10C
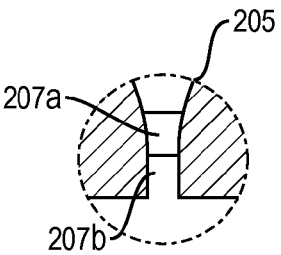
FIG. 10D

FLOW CELL

RELATED APPLICATION

This application claims the benefit of priority to U.S. Provisional Patent Application Ser. No. 61/702,532, filed Sep. 18, 2012, which is incorporated by reference in its entirety herein.

FIELD OF THE INVENTION

The invention relates to methods and apparatus for processing fluids, such as those methods and apparatus suitable for processing particles within a fluid sample and/or sorting particles based on predetermined characteristics.

BACKGROUND

Numerous approaches to particle processing as carried out by flow cytometers, cell sorters, and other cell separation systems have proven to be highly useful in such diverse life science applications as bioremediation, microbial fermentation, diagnostics, and other biomedical applications. Flow cytometers are systems that can measure large numbers of homogeneous or heterogeneous particle sets to achieve statistically relevant data sets that can be used to identify subpopulations within a given particle population. These measurements are often performed optically, or they may be electrical in nature when a stream of particles passes through an interrogation zone. With the addition of a sort functionality, a flow cytometer can further be used to isolate particle(s) of interest from a sample via operator control. This technique can be used to process particle populations as defined by the operator. One common cell separation method uses electrostatic forces to divert an electrically or electrostatically charged stream, droplet, or droplets containing a cell or cells having specific properties. The diverted cells are subsequently processed as appropriate to the particular application.

Conventional systems for processing particles typically rely on a number of nonintegrated fluidic components, which are unwieldy and may result in contamination problems. U.S. Pat. No. 6,079,836 discloses an example of a prior art particle processing system wherein several different components form the fluidic contact surfaces and surfaces contiguous to the droplet formation, sorting, and collection regions are not sealed from the external surrounding environment. For example, in conventional particle sorting systems, the particles to be sorted form a suspension in a liquid medium that passes through or is contained within a collection of fluid contact surfaces. In conventional droplet sorters, the suspension passes through a nozzle and is formed into a stream of droplets (the aerosol phase) before being captured in collection vessels. The droplet stream and associated aerosol can touch or contaminate any area within the system that is not sealed away from the stream. Crucially, in many particle processing applications, either or both of "operator isolation" and "product isolation" must be ensured. "Operator isolation" refers to protecting the operator from exposure to the particle suspension, for example, when there is a possibility of infectious disease agents or other noxious material existing within the suspension. "Product isolation" refers to isolation of the suspension from contamination with traces from outside the suspension, including contamination from the environment or from prior suspensions that have passed through the sorting system. Product isolation also refers to isolating the instrument from the product. Conventional sorting systems and other particle processing systems thus require operation in chambers (such as biohoods) to provide operator isolation. However, these types of systems are difficult to service as they require replacement and/or cleaning of all of the fluid contact surfaces in order to guarantee product isolation and the manual steps required represent a risk to personnel. Further, in a climate where ease of use is increasingly prioritized, such systems fall short.

SUMMARY

It is thus desirable to provide an easy to use flow cell that encapsulates all fluid contact surfaces and/or all fluid flows for use with particle processing technology. The encapsulation of the fluid contact surfaces provides for both operator isolation and product isolation.

According to certain aspects, the present invention may provide a fully enclosed flow cell for a particle processing system. Generally, the fully enclosed flow cell may be disposable. Optionally, the flow cell may be sterilizable and reusable.

According to some aspects, the present invention may be directed toward a flow cell including a sort chamber, which further includes a hydrodynamic focusing region; a sheath vessel; a first fluidic path; a sample vessel; a second fluidic path; a transducer placed external to but in communication with the sort chamber; an electromagnetic radiation source placed external to but in communication with the sort chamber; a plurality of transmission surfaces disposed in the sort chamber; at least one charged deflection plate disposed external to the sort chamber; a grounding element disposed external to the sort chamber; one or more orifices; and one or more collection vessels. The sheath and sample vessels may be selected from the group consisting of a rigid container and a flexible walled container. In one embodiment, two charge plates are provided.

According to other aspects, in another embodiment of the present invention, a flow cell is provided which includes a sort chamber, which further includes a hydrodynamic focusing region; a sheath vessel; a first fluidic path; a first flow control mechanism; a sample vessel; a second fluidic path; a second flow control mechanism; a transducer placed external to but in communication with the sort chamber; an electromagnetic radiation source placed external to but in communication with the sort chamber; a plurality of transmission surface transmission surfaces disposed in the sort chamber; at least one charged deflection plate disposed external to the sort chamber; a grounding element disposed external to the sort chamber; one or more orifices; and one or more collection vessels. The sheath and sample vessels may be selected from the group consisting of a rigid container and a flexible walled container. In one embodiment, two charge plates are provided.

According to further aspects of the invention, in certain embodiments, a flow cell is provided with an enclosed plurality of integrally-constructed regions in fluid communication with one another. The enclosed plurality of integrally-constructed regions may include a sort chamber having a jet-forming region, a particle interrogation region located downstream of the jet-forming region, and a droplet deflection region. The sort chamber may further include a focusing region, which may be located upstream of the jet-forming region. The sort chamber may include one or more electromagnetic radiation transmission surfaces operatively positioned with respect to the particle interrogation region.

The sort chamber may be enclosed. Further, the sort chamber may be operatively sealed, in that the sort chamber may be completely enclosed with the exception of one or more input and/or output ports or orifices that are sealed (or configured to be sealed) prior to the sort chamber being operatively engaged to a particle processing apparatus. Standard operating procedures (SOP) may be used to operatively engage the input and output ports to the particle processing system. Further, the sort chamber may be sterilizable, such that a sterile enclosed environment is available for fluid sample processing. The sort chamber may also be manufactured of relatively inexpensive materials and/or components such that the sort chamber may be considered disposable.

According to even other aspects of the invention, a particle sorting apparatus may include a flow cell having a fully enclosed fluidics system; a transducer placed external to but in communication with the flow cell; an electromagnetic radiation source placed external to but in communication with the flow cell; one or more transmission surfaces disposed on the flow cell; at least one charged deflection plate disposed external to the flow cell; and/or a grounding element disposed external to the cell. The flow cell may include a sample vessel and one or more collection vessels fluidically coupled to the flow cell and forming part of the fully enclosed fluidics system. Further, the flow cell may include a sheath fluid vessel fluidically coupled to the flow cell and forming part of the fully enclosed fluidics system. The sample, sheath and collection vessels may be selected from the group consisting of a rigid container and a flexible-walled container.

According to certain aspects, a further embodiment of the present invention provides an enclosed flow cell for particle sorting. In one embodiment, the particles are cells. The flow cell may include an integrated nozzle region, particle interrogation region, drop deflection region and sort stream collection region. A transducer in communication with the flow cell may cause the flow cell or a portion thereof to oscillate to thereby convert a fluid stream into a series of droplets. A charge field is generated in communication with the flow cell to achieve sorting, i.e., deflection of one or more of the droplets. In one embodiment, a jet-forming element is provided which forms entering particles into an exiting jet stream. An excitation source may be applied to the element before the jet enters, while the jet is being formed in the element (by means of optical transmission surfaces in the jet-forming element) or upon exiting the jet-forming element.

In one embodiment, the enclosed flow cell is manufacturable via machining techniques (subtractive fabrication). In another embodiment, the flow cell is manufacturable via additive fabrication. In another embodiment, the additive fabrication is selected from the group consisting of molding (including injection molding); three-dimensional printing; thermal expansion of compounds such as polymers; stereolithography; and sintering. The flow cell may be reusable or disposable. In yet another embodiment, the flow cell combines one or more of the preceding fabrication methods.

The present invention may further provide a kit for particle processing, preferably cell sorting, including an integrated flow cell fittable and removable from a sorter or other particle processing machine or system. The flow cell may be attached to a receptacle connecting to rigid-walled vessels or flexible walled vessels for fluid containment. The kit may further include flexible tubing between the flow cell and one or more of the receptacle vessels.

BRIEF DESCRIPTION OF THE DRAWINGS

FIG. 10 is a schematically illustrates a flow cell with a separately formed nozzle tip integrally joined to the sort chamber according to another illustrative embodiment of an aspect of the present invention.

Throughout the application, similar components of different embodiments of the particle processing flow cell may be designated with like reference numbers. The figures are not necessarily drawn to scale.

DETAILED DESCRIPTION

Figure 1:
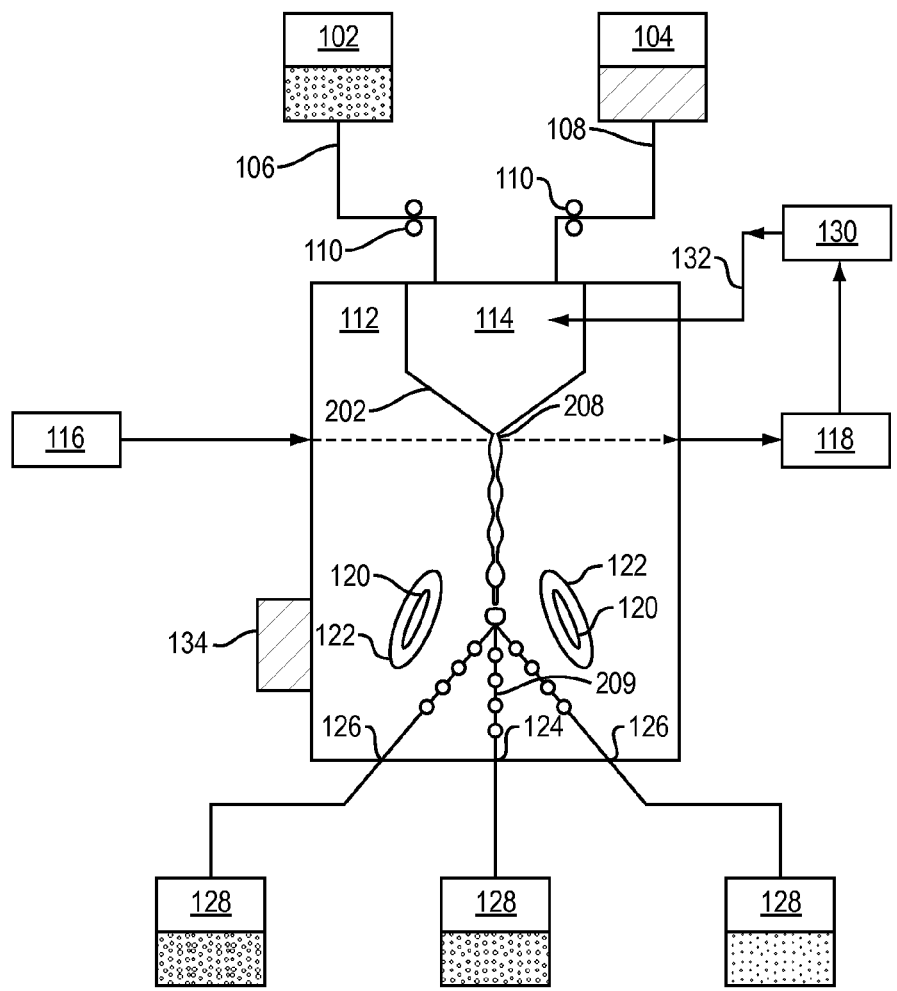
FIG. 1 schematically depicts a flow cell for particle processing according to an illustrative embodiment of an aspect of the present invention.

The present invention provides a flow cell for performing particle processing, such as particle sorting, on a sample. The present invention is described below relative to illustrative embodiments.

Those skilled in the art will appreciate that the present invention may be implemented in a number of different applications and embodiments and is not specifically limited in its application to the particular embodiments depicted herein.

As used herein, a "flow cell" refers to a collection of chambers and/or fluid pathways that are linked together as a single object that can be transported or moved as one piece. The flow cell may be formed of a plurality of components. Some of the components, such as chambers, in a flow cell may be substantially rigid, while other components, such as channels or tubes connecting chambers or vessels, may be flexible. A flow cell may have both microfluidic and droplet components.

As used herein, the term "sort chamber" refers to an enclosed element for handling, processing, ejecting and/or analyzing a fluid sample including at least one flow-path. A microfluidic sort chamber is a sort chamber including at least one flow-path having microscale dimensions. A flow-path having microscale dimensions refers to a flow-path having one or more cross-sectional dimensions in the range between 10 microns and about 1 mm. According to some embodiments, the flow-paths of a microfluidic sort chamber may have one or more cross-sectional dimensions between about 25 microns and about 250 microns and preferably between about 50 µm and about 150 microns. The forgoing ranges are intended to include the above-recited values as upper or lower limits. It is to be understood that not every flow-path dimension in a microfluidic sort chamber need be a microscale dimension, and thus, some flow-path dimensions in a microfluidic sort chamber may be greater than the microscale dimensions (e.g., on the order of 10 mm).

As used herein, "particle" may include those of biological interest such as cells, bacteria or viruses, organisms, or other naturally occurring or synthetically derived objects.

As used herein, "fluid contact surfaces" refers to reservoirs, tubes, chambers, vessels, nozzles, orifices, fittings and/or other elements which contact and/or are exposed to fluid in the flow cell.

"Sheath fluid" is used and understood to be interchangeable with "buffer solution" or "supernatant".

"Orifice" is understood to be any opening, hole, aperture, passage, etc. that has a reduced cross-sectional area relative to a chamber or channel with which it is in fluid communication. Thus, an orifice is understood to be dimensionally restricted relative to the chamber or channel with which it is in fluid communication. The cross-section of an orifice need not be constant, but rather may vary along its length. Thus, for example, according to some embodiments, an orifice may be characterized, for example, by a predetermined lead-in geometry or a predetermined lead-out geometry or both. Alternatively, the cross-section of an orifice may be constant along its length. An orifice may be any size or cross-sectional shape opening allowing fluid to move through it.

"Enclosed" is understood to mean wholly or partially contained within a three dimensional structure. "Completely enclosed" is understood to mean wholly contained within a three dimensional structure. According to certain aspects, the enclosing three dimensional structure may be integrally constructed and may even be monolithically constructed. The term "encapsulate" refers to enclosing, surrounding, isolating, encasing, and the like, as if in a capsule, enclosure, chamber, compartment, container, vessel, etc.

A "sealed" system or component is understood to mean any system, enclosure, chamber, compartment, etc. that may for practical purposes be closed so as to prevent the egress of such amounts of material as to cause a hazard or the ingress of such amounts of material as to cause contamination. An "operatively sealed" system or component refers to a system or component that is functionally isolated from an external environment during operation. Thus, an "operatively sealed" system or component may include one or more input and/or output ports that, when used according to a specific standard operating procedure (SOP), may be opened or partially opened to the environment prior to being operatively engaged to the particle processing apparatus, but which became part of a completely sealed system when operatively engaged to the particle processing apparatus. A "hermetically sealed" system or enclosure is functionally isolated, i.e., fluidically disconnected, from an external environment such that any contents within the sealed system may not be in direct contact with the environment. An airtight system is "hermetically sealed."

The terms "integral," "integrally-formed" or "integrally-constructed" generally refer to parts being maintained in a permanent, structural relationship as a single unit. "Integral" components cannot be separated from each other without damaging or breaking at least one of the components. As such, "integral" is not necessarily restricted to a one-piece article or a monolithically-formed article and is sufficiently broad to encompass constructions made up of a number of pieces that are united by adhesive, fastening, welding and other permanent attachment or joining means. In contrast, the term "monolithic" or "monolithically-formed" generally refers to a single-piece construction or fabrication that does not require attachment or joining of separately formed parts during the formation process. A monolithic article is seamless. Thus, a molded article, an article that is machined from a single piece of material, an article that is 3-D printed, etc. may be considered to be monolithic or monolithically-formed.

As used herein, "microfluidic" refers to a device, apparatus, component, etc. having at least one fluid channel, flow path, orifice, etc. having at least one cross-sectional dimension of less than 1.0 mm. The cross-sectional dimension of the channel or flow path is measured perpendicular to the direction of fluid flow within the channel. A "channel" is a feature that at least partially directs flow of a fluid. The channel may have any cross-sectional shape. Further, the cross-sectional dimensions, area, or shape of a channel may be constant or may vary along one or more portions of the length of the channel. Channels may be formed by any of various methods known in the art, for example, micromachining, laser ablation, film deposition, photolithography, etching, molding, 3-D printing, etc.

As used herein, the term "preform" refers to an element that has undergone some preliminary shaping so as to be provided with an approximate final shape, size or form, but is not yet in its final usable form. For example, a preform for a sort chamber may have the basic geometry of the ultimate sort chamber, including a hydrodynamic focusing region, but may be lacking an orifice or other feature to be provided in a subsequent process step. As another example, a preform for a nozzle tip may have the basic geometry of the ultimate nozzle tip, including a hydrodynamic focusing region, but may be lacking an orifice.

FIG. 1 illustrates a flow cell 100 for performing a process on a sample, having all fluid contact surfaces completely enclosed according to an illustrative embodiment of the invention. Sample fluid and sheath fluid (buffer solution) exit from sample vessel 102 and sheath vessel 104 respectively. Generally, the sample and sheath vessels are a rigid container or a flexible bag containing sufficient quantities of fluid to complete an intended sorting procedure. Alternatively, the processes may be carried out in the absence of sheath fluid. A flow cell 200 for processing particles in a stream may include an enclosed plurality of integrally-constructed regions in fluid communication with one another. The integrally-constructed regions may include a sort chamber 212 having a stream focusing region 114; a jet-forming region 202 located downstream of the focusing region 114; a particle interrogation region 208; and a droplet deflection region 209. Depending upon the constraints of the processing system, the particle interrogation region 208 may be located upstream of, downstream of, and/or at the jet-forming region 202.

Sample vessel 102 and sheath vessel 104 are in fluid communication with a sort chamber 112. Upon exiting the vessels 102, 140, the fluids subsequently enter a first fluidic path (sample fluid fluidic path 106 for the sample fluid and sheath fluid fluidic path 108 for the sheath fluid). One or more optional flow control mechanisms 110 may be present; the flow control mechanisms are intended to control the flow of fluid from vessels 102 and 104. In exemplary but non-limiting fashion, control mechanisms may be valves such as pinch valves and/or pumps, such as peristaltic or displacement pumps.

Sort chamber 112 receives input from sheath fluid (or buffer) vessel 102 and sample (includes particles to be processed) vessel 104 via a plurality of first ports or input ports. The sample and sheath fluids are introduced into the focusing region 114, establishing a core flow of entrained or suspended particles. In the sort chamber 112, sample and/or sheath fluid is focused in the focusing region 114); in one embodiment, the focusing process may be hydrodynamic, but may additionally or alternatively use optical tweezers, acoustic focusing or surface acoustic wave (SAW) technology to entrain particles.

Excitation source 116 may be disposed externally to sort chamber 112. Excitation light generated, for example, by a laser (or other suitable electromagnetic source) passes from outside the sort chamber 112 to inside the sort chamber 112 through a transmission surface such as a window (not shown). Transmission surfaces in the sort chamber 112 also allow scattered and/or fluorescent light to exit and are used to detect and/or analyze the particles and/or cells travelling inside the sort chamber 112. The excitation light may impinge on fluid located in the sort chamber 112 prior to, during, or after hydrodynamic focusing. One or more sensing elements 118 may be disposed externally to the sort chamber 112 as well. The sensing elements 118 may detect scatter, fluorescence, or other light, as appropriate.

The transmission surfaces may be integrally joined to the flow cell. The transmission surfaces may be provided as optical elements having any optical modality, including transmissive, reflective, refractive, diffractive, diffusing, filtering, and the like. According to some embodiments, the flow cell may be supplied with recesses or frames into which one or more of the optical elements may be inserted or housed. According to other embodiments, the optical elements may be embedded within the flow cell. For example, the optical element may be a fiber optic cable embedded in the wall of the flow cell. Optionally, according to some embodiments and depending upon the material used to form the detection region, the transmission surfaces may be monolithically formed with the detection region of the flow cell.

Further, one or more charge plates 120 may be disposed externally to the sort chamber 112. Charge plates 120 create an electrostatic field within the sort chamber 112. In the embodiment shown in FIG. 1, the charge plates 120 rest within or are accommodated by access regions 122 formed in a non-enclosed region of sort chamber 112. Access regions 122 may be configured to complementarily match the profile and mounting configuration of the charge plates 120. Further, access regions 122 may provide for a sliding-fit interface, a friction-fit interface, a spring-loaded interface, a clamped interface, a snap-fit interface, etc. with externally supplied charge plates 120. The externally supplied charge plates may be provided on the particle processing system. Yet further, the charge plates and/or associated componentry may be used as a mounting and/or reference surface for holding indefinitely or replaceably an enclosed flow cell. Additionally, this mounting system may allow motion and accurate positioning of the flow cell with respect to certain external 'items' such as an excitation source. Thus, according to some embodiments, the externally supplied charge plates (and/or optionally the grounding element) may provide movable mounting plates, which may be configured to bring the flow cell quickly, easily and reliable into optical, acoustical, and/or electrical alignment.

One or more grounding elements, if any, may be disposed externally of the sort chamber 112, and if desired, grounding access regions may be provided to accommodate the one or more externally disposed grounding elements. Similarly to the charge plate access regions 122, grounding element access regions may be configured to complementarily match the profile and mounting configuration of the grounding elements. Further, the grounding element access regions may provide for a sliding-fit interface, a friction-fit interface, a spring-loaded interface, a clamped interface, a snap-fit interface, etc. with the externally supplied grounding elements. The externally supplied grounding elements may be provided on the particle processing system.

Additionally, a transducer 134 may be disposed on an external surface of the sort chamber 112. For example, a transducer 134 which vibrates the sort chamber 112 at a known and controlled frequency thereby inducing the fluid stream in the sort chamber 112 to break into individual droplets may be provided. The droplets that are to-be-charged are charged at the exact time that the droplet breaks from the sort fluid stream, resulting in a net charge on the surface of a given droplet. Any transducer as would be known to persons of ordinary skill in the art for producing droplets may be provided. Further, the transducer 134 may be securely butted up against an external surface of the flow cell, particularly, up against an external surface of the sort chamber. Optionally, transducer access regions may be configured to complementarily match the profile and mounting configuration of the transducer 134, and these transducer access regions may provide for a sliding-fit interface, a friction-fit interface, a spring-loaded interface, a clamped interface, a snap-fit interface, or other coupling mechanism, etc. with the externally supplied transducer 134. Transducer coupling may be further improved through the use of gels or other acoustic matching materials.

Additional, or alternative, transducers may be provided. According to certain aspects, transducers for focusing the fluid stream prior to excitation may be provided. As one example, an ultrasonic transducer may be provided. As another example, one or more surface acoustic wave generators, such as interdigitated transducers (IDTs), may be provided. According to other aspects, a transducer for sorting the particles in the fluid stream into a particular collection vessel may be provided. As one example, one or more surface acoustic wave generators (for forming either standing or streaming acoustic waves) may be provided. In some aspects the transducers may be integrally joined to or provided within the flow cell; in other aspects, they may be externally provided.

Processor 130 may also be disposed externally to the sort chamber 112. Processor 130 receives input from sensing element 118 and based upon desired characteristics of particles (or droplets) of interest for sorting causes charge (voltage) to be applied via charge path 132. In an optional embodiment, a portion of a processor 130, such as a FPGA may be supplied with the flow cell and/or sort chamber and this "on-board" portion of the processor may interface with the externally disposed processor 130. This may be particularly useful should the flow cell be configured to accommodate specialized unit processes.

Generally, excitation source 116, sensing elements 118, charge plates 120, grounding elements, transducer 134, and/or processor 130 may be disposed externally to the flow cell and operatively engaged to the flow cell when the flow cell is operatively engaged to the particle processing system.

According to certain aspects, the droplets travel through the sort chamber 112 within a droplet deflection region and are exposed to an electrostatic charge field. When a droplet enters the electrostatic field, depending on its charge, it may be deflected and travel into a selected fluidic sort or collection path 126. Alternatively, the droplet may continue undeflected, or only slightly deflected, into another fluidic sort or collection path 124. The fluidic paths 124, 126 terminate into a plurality of second ports or outlet ports. The fluids within fluidic sort or collection paths 124, 126 exit into a plurality of collection vessels 128. Once the sorting procedure is completed, one or more of the vessels 128 may be removed or disconnected from the sort chamber 112 and kept for further processing.

During droplet formation undesirable aerosols or microdroplets may be formed. These microdroplets, whether charged or not, may be dispersed throughout the droplet deflection region and may eventually come into contact with or land on a surface forming the droplet detection region. Thus, one or more of the surfaces forming the droplet deflection region may be provided with means for controlling these microdroplets. For example, the means for controlling the microdroplets may include directing the microdroplets into a predetermined collection vessel. For example, a surface forming a portion of the droplet detection region may be provided with one or more micro channels or ridges for collecting and channeling the microdroplets into the collection vessel. As another example of a means for directing microdroplets, a surface forming a portion of the droplet detection region may be provided with a coating, such as a hydrophobic coating to facilitate the beading and eventual runoff of the microdroplets into the collection vessel. As even another example, one or more of the surfaces may be provided with a surface texture for capturing and retaining microdroplets. Yet a further example may utilize electrostatic charge properties of the microdroplets in combination with one or more charged surfaces that may be used to attract these microdroplets and combine this with a suitable collection means, surface, channel, or other pooling method.

Mechanisms may be provided, in one embodiment, an aseptic method, for connecting, removing, or reconnecting sort chamber 112 to vessels (sample, sheath, keep, waste, etc.). Example mechanisms include removable plugs, resealable plugs, septums, membranes, luer locks, sealable ports, or other connection and/or disconnection devices as would be known to persons of ordinary skill in the art. These mechanisms may be configured to maintaining the sterility of the fluids and to minimize exposure to the environment, particularly when removing sample and sorted fractions from the flow cell. Pneumatic inlets and outlets, if any, may be provided with filters (e.g. 0.22), membranes, or other sealable ports. The remainder of the flow cell, as well as one or more of the vessels, may be reused, re-sterilized or disposed of as desired.

It is further contemplated that sheath or buffer fluid may be recycled and or reused. Recycling systems may be pump based or pneumatic. A portion of fluid from any of vessels 128 or from any of the collection paths 124, 126 may be used for this process. Further, by removing fluid from vessels 128 or collection paths 124, 126, particle concentration may be altered. According to some embodiments, one or more recycle paths may extend from a collection path to the sample fluid inlet port and/or to the sheath fluid inlet port. The recycle fluid flow paths may be monolithically formed with the flow cell, separately formed relative to the remainder of the flow cell and then subsequently integrally attached to the flow cell, or separately formed and configured to be optionally attached to the flow cell. The recycle fluid flow paths may be in fluid communication with and/or operatively engaged to fluid control elements such as valves, pumps, etc., and to separation elements such as filters, membranes, secondary sorters, etc.

Further, separate components of the flow cell may be made of the same material or different materials. The flow cell may be manufacturable via additive fabrication, which those of skill in the art understand may include, without limitation, overmolding; injection molding; fused deposition molding; casting; three-dimensional printing, including powder bed, inkjet heat and plaster-based three dimensional printing; thermal expansion of compounds such as polymers; stereolithography; direct metal laser sintering; laminated object manufacturing; electron beam melting; selective laser sintering.

In a preferred embodiment, the flow cell may be disposable. In an alternative embodiment, the flow cell may be reusable. For particular purposes, it may be desirable to provide for a sterile flow cell.

Figure 2:
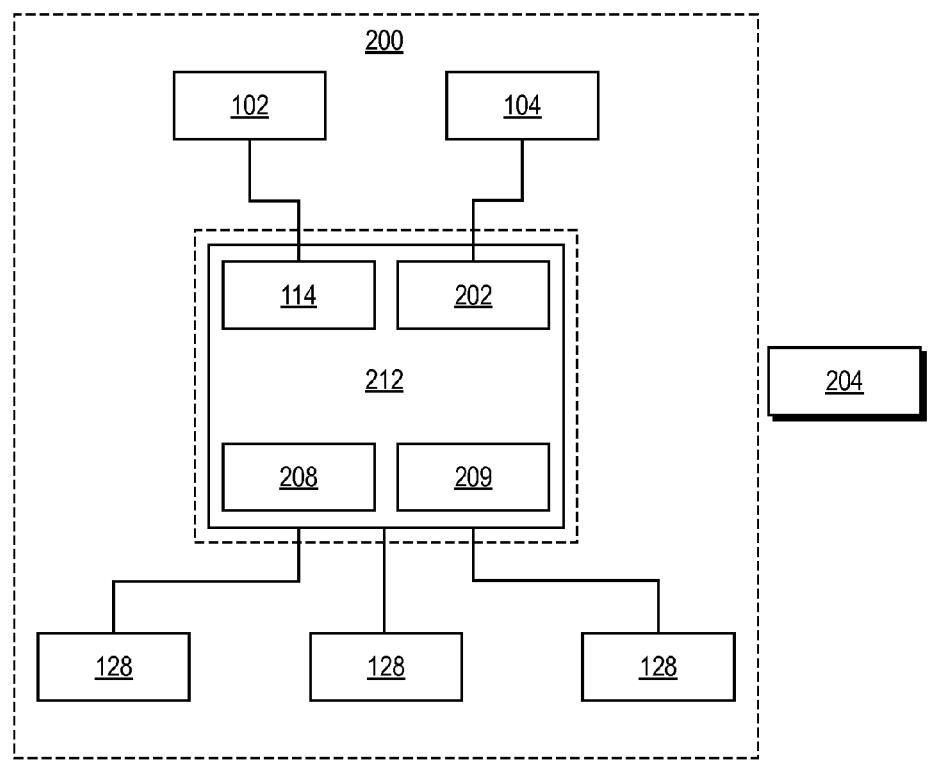
FIG. 2 provides a block diagram of a flow cell for cell sorting according to an illustrative embodiment of an aspect of the present invention.

FIG. 2 shows a block diagram of a flow cell according to another illustrative embodiment of the present invention. In this embodiment, flow cell 200 includes nozzle 202. In the present disclosure, a nozzle is a component or portion of a component that hydrodynamically focuses fluid flowing therethrough just prior to the fluid flowing through an orifice 205. The downstream portion of a nozzle 202 may be referred to as a nozzle tip 203. The nozzle tip 203 includes an orifice 205 through which the hydrodynamically-focused fluid exits the nozzle 202.

According to aspects of the invention, the nozzle 202 and/or the nozzle tip 203 may be integrally provided with the flow cell 200. Additionally, according to certain embodiments, the nozzle 202 and/or the nozzle tip 203 may be monolithically formed with the flow cell 200. Alternatively, according to certain embodiments, the nozzle 202 and/or the nozzle tip 203 may be formed separately from the remainder of the flow cell 200 and subsequently integrally joined thereto to create the finished flow cell 200.

Certain prior art microfluidic chips are formed from a plurality of layers that are stacked or built-up perpendicular to the direction of flow through the orifice 205. This perpendicular stacking may limit the geometry of the flow paths, and particularly may limit the geometry of any hydrodynamic focusing region and of any orifice. In contrast, the techniques of the present disclosure advantageously enable the production of low cost, easily sterilized, disposable sort chambers which include an orifice suitable, for example, for fluid jet formation (such as in a droplet sorter or in a flow cell), or sample injection or hydrodynamic focusing (such as in a non-droplet flow cytometer). Materials used in forming the sort chamber may include, for example, any thermosetting or photo-curing resin, high performance engineering polymers, engineering polymers, standard polymers whether crystalline or amorphous or the like. The sort chamber may be molded at this step by an injection molding technique, such as by thermoplastic injection molding or by thermoset injection. The material for molding may be selected from polycarbonate, Pyrolytic carbon (PYC), a plastic, polymer, plastomer, epoxy, phenolic, Diammonium phosphate (DAP) and thermoplastics such as nylon, acetal, Polybutylene terephthalate (PBT), Polyphenylene oxide, Polyphenylene sulfide, or other similar materials. Those familiar in the art would be aware that other suitable polymers, resins, or other moldable materials could be used herein. Optionally, the sort chamber may be formed via fused deposition molding, such as in a 3-D printer.

In exemplary embodiments, it may be desirable to have the sort chamber exhibit low autofluorescence properties. Common examples of thermoplastic resins that are known to have low autofluorescence properties include cyclic olefin copolymers (COC), Poly(methyl methacrylate) (PMMA), and the like. In exemplary embodiments, the materials used in forming the sort chamber may advantageously allow for photo-excitation (for example, fluorescent excitation) or photo-collection (for example, imaging) of a sample or of other fluidic elements through the walls of the sort chamber. COC, Cyclic Olefin Copolymer (COP) and PMMA are examples of materials with high transmission rates in wavelengths of interest (for example, 350-900 nm) which would allow for photo-excitation or collection through the walls of the sort chamber.

A preform for the sort chamber may be formed using, for example, injection molding, thermoforming, compression molding, blow molding, vacuum forming, 3D printing and the like. Fabricating the sort chamber's preform may include defining various basic features of the sort chamber, for example, size, shape, configuration, flow-through regions, and the like.

According to certain aspects, finer features such as may be required for an orifice may be formed or otherwise defined in the sort chamber using a subsequent processing step, i.e., as a separate process from the act of fabricating the preform of the element. For example, an orifice may be created in the sort chamber's preform using an electromagnetic radiation process commonly referred to as "laser ablation" or "laser drilling." In other words, after initial formation of the sort chamber of the flow cell, an orifice may be formed in a nozzle region of the sort chamber by laser ablation (for example, laser drilling).

Laser ablation involves the concentration of a high power density of electromagnetic radiation, e.g., collimated electromagnetic radiation. In exemplary embodiments, the laser ablation radiation may be directed or focused with respect to a particular target on the perform of the sort chamber, for example, after an alignment operation which aligns the location of the desired orifice and the orifice forming device relative to features optically or mechanically identified on the preform. Mechanisms or means for forming orifices other than laser ablation, such as mechanical drilling, piercing, water jet cutting, grinding, turning, etching, electron beam machining and or lithography, ultrasonic machining etc. as would be known to persons of ordinary skill in the art, may be used to form or partially form the orifices in the preform. Further, if desired, such processes may be used to form other relatively fine features.

According to certain aspects, the electromagnetic radiation may be directed or focused from one or more directions with respect to the preform and the inlet or exit of the orifice. For example, in some embodiments, electromagnetic radiation may be directed or focused from the inlet side, from the exit side or from both.

Advantageously, according to the present disclosure, an electromagnetic radiation process may be used to define various features of the orifice, including, for example, defining lead-in or lead-out geometries thereof (see FIG. 10(d), items 207a, 207b). The specific lead-in and/or lead-out geometry of the orifice may be provided as a function of laser power, beam geometry and intensity pattern, location of the focal point, angle of the beam, etc. The configuration of the orifice may advantageously be used to provide a desired or predetermined flow profile through the orifice, for example, for focusing or aligning a stream of particles in a sample and/or for controlling or affecting droplet formation. See for example, U.S. Provisional Patent Application Ser. No. 61/879,379, filed Sep. 18, 2013, which is incorporated by reference in its entirety herein.

Laser ablation may be used to drill through a wall of the sort chamber's preform that may be up to several millimeters in thickness. In exemplary embodiments, the wall thickness of the preform for the sort chamber where the orifice is to be located may be less than 2 mm, less than 1 mm, and preferably less than or equal to 500 microns. In some embodiments, the wall thickness of the preform in which the orifice is to be formed may be between 50 to 400 microns thick, between 100 to 300 microns thick, or even approximately 250 microns thick. As further non-limiting examples, the wall thickness may be greater than 100 microns, preferably between 100 and 400 microns, or in some embodiments, between 100 and 300 microns. For example, the thickness of the wall wherein the orifice 205 is formed may be approximately 150 microns (e.g., 150 microns plus/minus 15 microns), approximately 200 microns (e.g., 200 microns plus/minus 20 microns), or approximately 250 microns (e.g., 250 microns plus/minus 25 microns).

Exemplary electromagnetic beam geometries which may be used in the ablation process may include elliptical, square, cylindrical, rectangular, polygonal, Gaussian, top hat (flat top) and the like. One or more transverse electromagnetic laser modes may also be utilized to produce the desired orifice such as $TEM_{00}$, $TEM_{01}$, $TEM_{10}$, $TEM_{20}$, $TEM_{02}$, etc. The focal point may be a steady or variable focal point and may be before (i.e., in front of), at, or after (i.e., behind) the surface of the preform's wall. Different beam geometries, pulse durations, focal points and intensity patterns may be used to create the desired orifice geometries. See for example, T. C. Chen and R. B. Darling, Fundamentals of Laser Ablation of the Materials Used in Microfluiducs, Micromachining Techniques for Fabrication of Micro and Nano Structures, Dr. Mojtaba Kahrizi (Ed.), InTech, pp. 35-60 (2012), which is incorporated by reference in its entirety.

The preform for the sort chamber may be aligned within a fixture (for example, using optical or mechanical alignment means, or both) relative to an orifice forming device. The alignment of the preform within the fixture may advantageously result in or enable the alignment of an electromagnetic radiation ablation device (or other orifice forming device) relative to the preform. The alignment of the orifice may be relative to a flow path extending longitudinally within the sort chamber. This flow path may be defined by an internal flow surface of the sort chamber, for example, a hydrodynamic focusing region 114a (see for example, FIG. 10(c), wherein a hydrodynamic focusing region 114a is shown for a separately formed nozzle tip 203') which may be located upstream of and just prior to the orifice inlet. It may be desirable to align the orifice with respect to the upstream hydrodynamic focusing region such that no internal discontinuities exist in the immediate vicinity of the orifice. In one exemplary embodiment, the upstream internal surface of the flow path of the sort chamber has a converging geometry and the orifice has a cylindrical geometry. The downstream cross-sectional geometry of the converging geometry may be the same as the cross-sectional geometry at the inlet of the cylindrical orifice. Alternatively, and/or additionally, the orifice may be aligned with respect to an external surface or feature of the sort chamber. In such instance, the external alignment feature may also be closely controlled with respect to the internal surfaces upstream of the orifice.

According to other embodiments, it may generally be sufficient to align the centerline of the orifice to within 50 microns of the centerline of the immediately adjacent upstream internal surface. Optionally, for better control of the fluid stream exiting the orifice, it may be desirable to more precisely align the centerline of the orifice to the centerline of the immediately adjacent upstream internal surface. For example, aligning the orifice centerline to within 40 microns, 30 microns, 25 microns, or even to within 20 microns of the centerline of the upstream internal surface may facilitate the creation of a well-behaved fluid stream exiting the orifice.

Even further, having the centerline of the orifice angularly aligned to within 20 degrees or less of the centerline of the immediately adjacent upstream internal surface may minimize spray, misalignment, or other undesirable characteristics of the exiting stream. According to some embodiments, more closely controlling this angular alignment to within 15 degrees, 10 degrees, or even to within 5 degrees may be preferable. Alternatively and/or additionally, angularly aligning the centerline of the orifice to within 20 degrees, 15 degrees, 10 degrees, 5 degrees, 2 degrees, one degree, 0.5 degrees, 0.1 degrees or even to within 0.01 degrees of an external surface and/or mounting feature of the sort chamber may provide useful control over the characteristics of the exiting stream.

According to some embodiments and as mentioned above, the orifice may be ablated from the upstream fluid flow direction (i.e., the ablating beam is traveling in the direction of fluid flow). Discontinuities where the upstream hydrodynamic focusing region meets the orifice may be minimized by matching the size and shape of the cross-section at the downstream end of the hydrodynamic focusing region to the size and shape of the upstream end of the orifice. The cross-section of the orifice may be circular and constant along the entire length of the orifice. The circularity of the orifice may be maintained to within a tolerance zone of less than 10 microns, less than 5 microns, or even less than 2 microns. The circularity of the cross-section of the downstream end, i.e., the exit hole, of the orifice may be maintained to within a tolerance zone of less than 10 microns, less than 5 microns, less than 2 microns, less than 1 micron or even less than 0.5 microns. The downstream exit hole of the orifice may be chamfered or provided with rounded edges. Optionally, the downstream exit hole of the orifice may be provided as a sharp, non-chamfered edge. The geometry of the exit hole of the orifice affects the accuracy and cleanness of jet, droplet formation, and subsequent droplet travel.

According to certain embodiments, the orifice may have a circular cross-sectional shape with a diameter within the range of 10 microns to about 500 microns, more preferably between about 25 microns and about 250 microns and most preferably between about 50 microns and about 150 microns. For some embodiments, the orifice may have a diameter of less than or equal to 100 microns. For other embodiments, the orifice may have a diameter of less than or equal to 85 microns or even less than or equal to 50 microns. The orifice diameter may vary by plus/minus 10%, but may preferably vary by only plus/minus 5%. Further, flaws or imperfections in the orifice may be limited to less than 5 microns, less than 3 microns, or even less than 2 microns.

According to other embodiments, the orifice may have a length within the range of 50 to 400 microns. Depending upon the characteristics of the fluid stream and the particles, it may be desirable to limit the length of the orifice to less than 250 microns, less than 200 microns, or even less than 175 microns. Additionally, it may be desirable for the length of the orifice to be at least 75 microns, at least 100 microns, or even at least 125 microns. According to some embodiments, advantageous control over the fluid stream may be achieved with an orifice having a length between 100 to 200 microns.

According to certain aspects, an internal surface geometry (see, for example, FIG. 10(c) showing an internal surface 114b for a separately formed nozzle tip 203')) provided by the preform upstream of the orifice that is conical, elliptical, or some other profile may be implemented that assists with fluidic performance characteristics of the sort chamber. Alternative geometries may be used that are well suited for particular particle types flowing through the sort chamber. In a non-limiting example, particle or cell orienting features may be formed during a primary and/or during a secondary formation step, for example during molding of a preform and/or during post processing thereof.

Thus, according to certain aspects, the internal surface geometry of the preform may provide a hydrodynamic focusing region upstream of the orifice. In some embodiments, elliptical and/or fluidic torsional regions that apply forces to particles in a particular manner may be formed for orienting sperm cells or other asymmetric or symmetric particles. For example, a fluidic torsional region may generate single torsional hydrodynamic forces having a hydrodynamic axis when a flow containing a particle sample stream passes through it. When the sample stream passes through this fluidic torsional region, particles within the sample may become radially aligned with respect to the hydrodynamic axis. The fluidic torsional region may also cause the sample to accelerate. See for example, U.S. Provisional Patent Application Ser. No. 61/879,379, filed Sep. 18, 2013, which is incorporated by reference in its entirety herein.

The overall shape of the fluidic torsional region may gradually taper as it extends downstream. The taper may be constant (i.e., linear) or varying (i.e., non-linear or curved). Further, the degree of curvature of the internal surface within the fluidic torsional region need not be constant. Since the fluidic torsional region is gradually and continually tapered, the cross-sectional areas may monotonically decrease as the fluidic torsional region extends downstream.

The tapered fluidic torsional region may be provided with a generally "elliptical" cross-section (i.e., a cross-section having a major axis and a minor axis that are not equal). The shape of the generally "elliptical" or elongated cross-section need not be constant as the fluid torsional region tapers as it extends downstream. According to certain embodiments, the ratio of the major to the minor axis may change and/or the curvature along the "elliptical" perimeter in the plane of the cross-section may change. For example, at the most upstream end of the fluidic torsional region, the cross-section may be generally circular. As the fluidic torsional region extends toward the downstream end, the cross-sectional shape may first become more elliptical (i.e., the ratio of the major to minor axis may become larger), and then become less elliptical (i.e., the ratio of the major to minor axis may become smaller), until at the most downstream end of the fluid torsional region (i.e., at the entry to the orifice) the cross-sectional shape has become substantially circular. See for example, the top plan and cross-section views of FIG. 10(c).

Coatings may also be applied to the sort chamber to advantageously alter the surface properties of the sort chamber. For example coatings may be used to impact lubricity, increase or decrease hydrophobicity (allowing for contact angle modifications), improve sterility, facilitate light protection and/or containment, and/or adjust optical properties such as preventing or inhibiting autofluorescence. Coatings for lubricity may include, for example, graphite, molybdenum disulfide, hexagonal boron nitride, tungsten disulfide and the like. Coatings for contact angle modification may be intended to increase or decrease hydrophobicity and/or may improve (decrease) the tendency for gas bubbles to stick to the surface and may include, for example, biopolymers and films and the like. See, e.g., Sol-Gel Technologies for Glass Producers and Users 2004, pp. 187-194 "Hydrophilic Coating Materials" by H. Schneider, N. Niegisch, M. Mennig, and H. Schmidt, which is hereby incorporated by reference. Coatings for improving sterility may include, for example, silane-based coatings, silver-based coatings, triclosan-based coatings or other anti-microbial coatings. Coatings for light protection and/or containment may include, for example, any material that is opaque to the wavelength(s) of interest, for example, 350-900 nm. Many metals are commonly used and may be applied by sputtering, painting, a metal particle suspension, etc. Certain metal coatings could also be used to suppress autofluorescence. Non-fluorescent coatings may include COC, COP, PMMA plastics and the like.

In some embodiments, following the initial molding step, the sort chamber may undergo post processing including, but not limited to, washing, curing, machining, coating, glazing, sterilizing, chemical treatments, laser etching, laser detailing, finishing processes, or other post molding processes. Optionally, the sort chamber may be subjected to an additional co-molding or overmolding step. For example, should a nozzle tip 203' (see FIG. 10) be separately formed with a ceramic, quartz, a jewel, etc. orifice subcomponent (not shown), the nozzle tip 203' may be joined by overmolding the orifice subcomponent so as to integrally form an upstream hydrodynamic focusing region 114*a* as part of the nozzle tip 203'. An additional post processing step may further include packaging and/or sterilization steps. The sort chamber and/or flow cell may be sterilized before or after packaging or both, for example, using gamma radiation, gas treatments, vapor and/or fluid exposure, temperature, or other sterilization techniques. The packaging may advantageously preserve the sterility of the flow cell.

Overmolding may generally involve a second component of a sort chamber being molded with respect to a previously formed first component of the sort chamber. By way of an example, a complimentary second portion of a sort chamber may be over molded with respect to a first portion of the sort chamber. For example, a separately formed nozzle tip 203' may be overmolded to the remainder of the sort chamber. The overmolding process may also be referred to as insert molding. The overmolding process may also include co-molding wherein two previously formed components or preforms of components of the sort chamber are place into a mold and co-cured.

Sort chamber components which may be overmolded relative to the bulk of the sort chamber may include, for, example, an injection tube, an oscillating element, a piezoelectric element, a nozzle housing, a charge pin, an electrical cable, an electrical connector, a nozzle alignment mechanism, a particle alignment mechanism, a sheath inlet connector, a sheath inlet tube, a sample inlet connector, a waste tube, a metallic element, a ceramic element, an optical window or other optical element, a fastener, and a seating element to thereby form the ultimate sort chamber. Optical elements may also be provided, for example for, photo-excitation or photo-collection, for example of a sample, through a wall of the sort chamber. Examples of optical elements may include transmissive, reflective, refractive, diffractive, diffusing, or other elements providing optical modalities. These optical features may be used to focus, capture, split, diverge, manipulate and/or transmit light (i.e., electromagnetic radiation) in some other useful manner associated with the measurement of the fluid or the particles in the proximity of the jet-forming element 306 and/or orifice 205.

Referring to FIG. 10, a separately formed nozzle tip 203' may be provided with a substantially cylindrical or other non-tapered outer wall section toward the upstream end and a substantially conical or other tapered outer wall section converging toward the downstream end. The non-tapered section may facilitate association of the nozzle tip 203' with the sort chamber. For example, the upstream end may be inserted into a complementarily shaped recess of the sort chamber. In some embodiments, the preform of the sort chamber may define an internal flow path or channel for hydrodynamically focusing the fluid flow just prior to entering the orifice. This pre-orifice focusing region may be characterized by a substantially cylindrical geometry or other non-tapered geometry, a substantially conical geometry or other tapered geometry, a substantially cylindrical geometry or other non-tapered geometry followed by a substantially conical geometry or other tapered geometry, or other combinations thereof.

The overall dimensions of a separately formed nozzle tip 203' may be on the order of centimeters or, preferably, millimeters. For example, the nozzle tip 203' may be approximately 13 mm in length and may have a width or diameter of approximately 6 mm. Nozzle tip 203' may define an internal flow path characterized by a substantially conical geometry (for example, having a cone angle $\alpha$ between 15 and 45 degrees or, for certain applications, a cone angle $\alpha$ of approximately 23 degrees).

In exemplary embodiments, a separately formed nozzle tip 203' may include alignment aids, e.g., optical or mechanical elements (for example, slots, flanges, coating strips and the like) for facilitating alignment with and insertion into the flow cell 200.

Conventional materials for fabricating nozzle tips 203', including ceramics, glass, quartz, fused silica, or precious stones such as jewels, may be used. The nozzle tip 203' may be inserted or joined to the remainder of the flow cell 200 using any suitable technique, including, for example, fusing, bonding, co-molding, overmolding, etc. According to other aspects, the materials used in fabricating a separately formed nozzle tip 203' may be considerable softer than conventional materials used for forming nozzle tips and/or orifice elements. Conventional materials, such as ceramics, quartz, glass etc., have a high hardness, which provides excellent durability and wear resistance. Thus, orifices formed from such high hardness materials retain their dimensional tolerances even after repeated use. For example, ceramics generally have a Vickers hardness of greater than 2000. Quartz may have a Vickers hardness of greater than 1000. Glass may have a Vickers hardness of greater than 500. Metals may have a Vickers hardness ranging from 50 to 1000, depending upon their elemental composition, their worked form, and their annealing or work hardening. On the other hand, polymers generally have a Vickers hardness less than 200, and in many instances, less than 100, and in some instances less than 50. For example, PMMA has a Vickers hardness less than 20. Softer materials such as polymers allow for ease of manufacture, while at the same time being suitable for a single use, disposable, nozzle tip 203. Materials having a Vickers hardness less than 500 may provide sufficient ease of manufacture as to be cost effective. Materials having a Vickers hardness less than 200 may be preferred.

Referring back to FIG. 2, item number 204 is the interface between the flow cell 200 and its external environment (e.g. instrument/control system). The interface may allow for the flow cell 200 to be easily fittable and removable. Thus, for example, the interface 204 may include a mounting holder with interfacing components (e.g., excitation and/or sensing elements, transducers, charge plates, grounding plates, etc.) mounted thereto.

Figure 3:
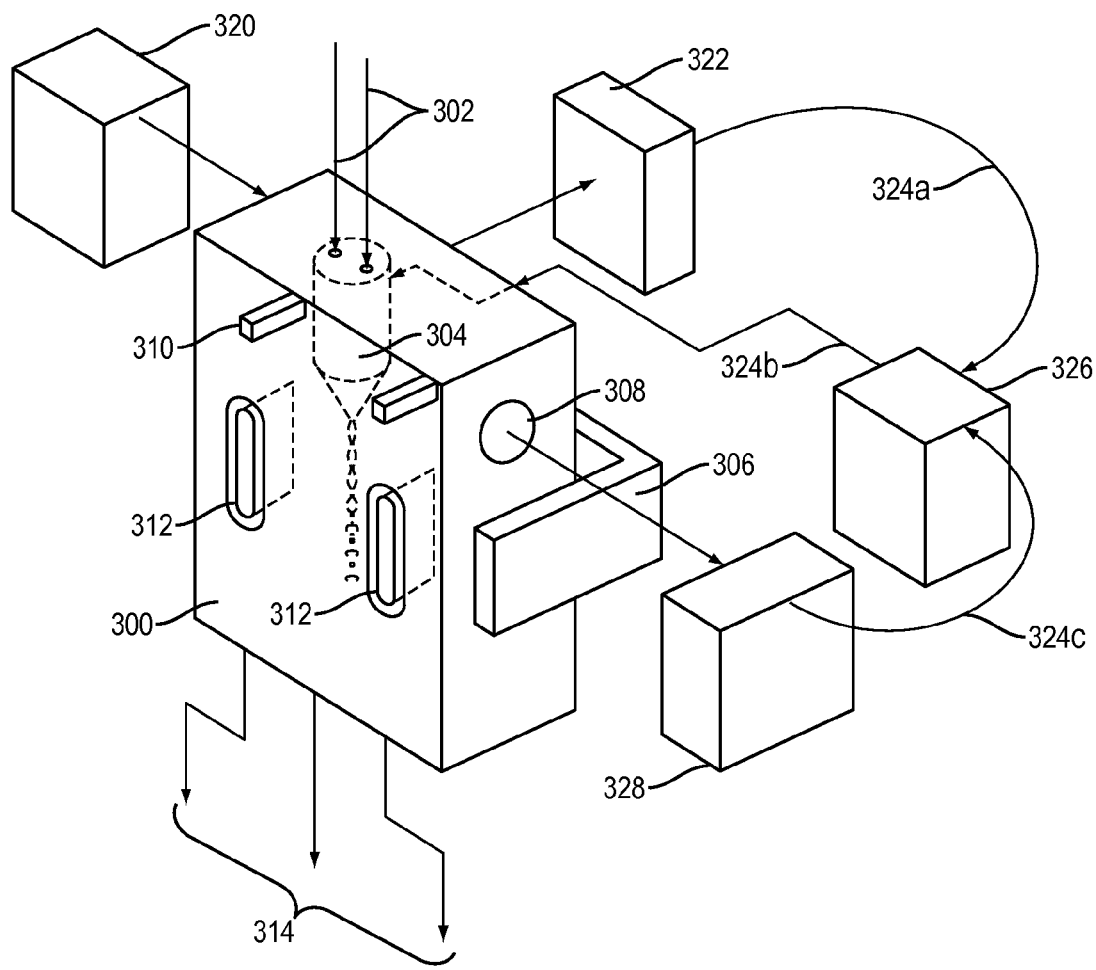
FIG. 3 is an exploded schematic view of a flow cell for cell sorting according to an illustrative embodiment of an aspect of the present invention.

FIG. 3 depicts a flow cell of the present invention in an embodiment particularly appropriate for cell sorting. Enclosed flow cell 300 includes a set of entry ports 302 for sample and sheath fluid; a nozzle region 304 terminating in an orifice and integrated with a sort chamber; a mounting region 306; one or more optical transmission surfaces 308; grounding element 310; charge plates 312; and exit ports 314. Disposed externally to the enclosed flow cell are excitation source 320; and a first sensing element 322, which sends signal 324A to processor 326 which in turn sends charge signal 324B to jet region 330 in nozzle region 304. Optical transmission surface 308 permits transmission to a second sensing element 328 which sends signal 324C to processor 326.

Figure 4:
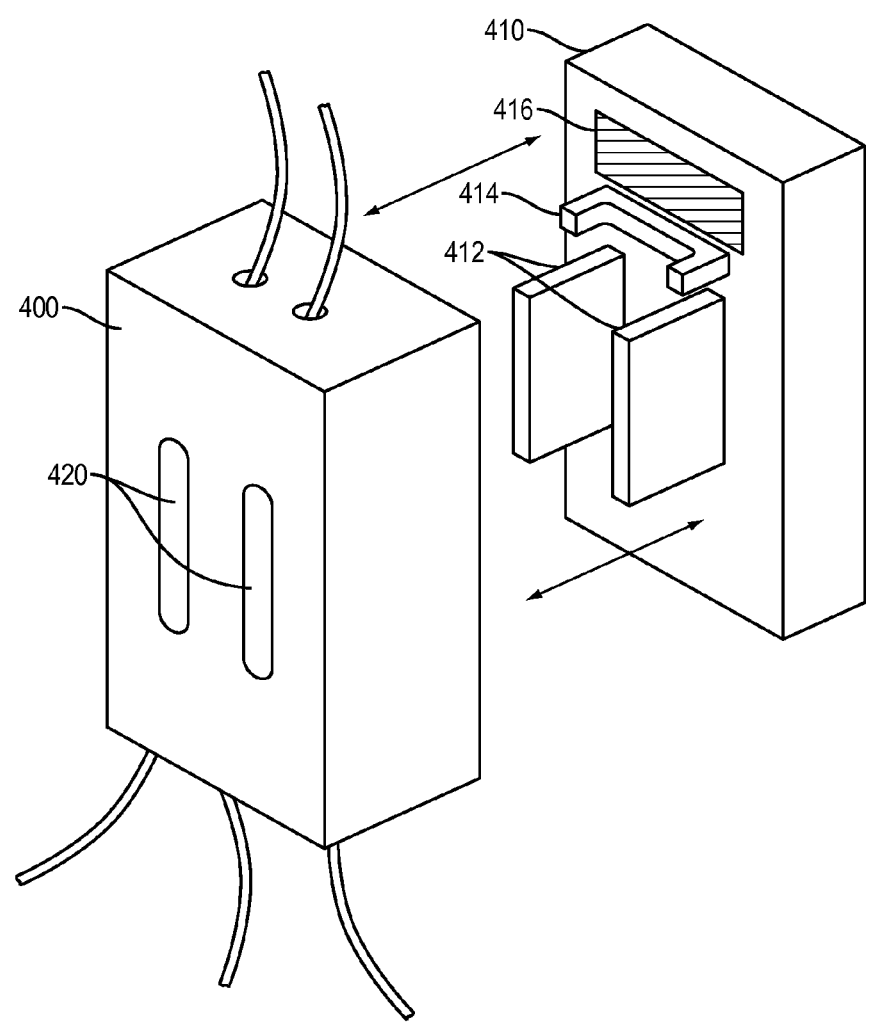
FIG. 4 schematically depicts a flow cell and holder according to an illustrative embodiment of an aspect of the present invention.

FIG. 4 depicts a flow cell and holder according to an illustrative embodiment of the present invention. Enclosed flow cell 400 is disposed upon communication/control element 410. Externally disposed charge plates 412 fit into access region 402 which may be provided as recesses or as complementarily-shaped regions in or on flow cell 400. Externally disposed grounding element 414 fits into a recess or a complementarily-shaped region of flow cell 400 as well. Similarly, externally disposed transducer 416 may be fitted upon flow cell 400. Other externally disposed elements, as would be known by persons of ordinary skill in the art (e.g., electrical connectors, heaters, stirrers, etc.), may be provided for operationally interfacing with the flow cell. Each of these externally disposed items (charge plates 412, grounding element 414, transducer 416, connectors, heaters, etc.) may be fitted upon communication/control element 410. In one embodiment, magnets are used to attach the flow cell 400 to the mounting region. Other fastening elements are contemplated as well and are within the scope of the present invention.

Figure 5A:
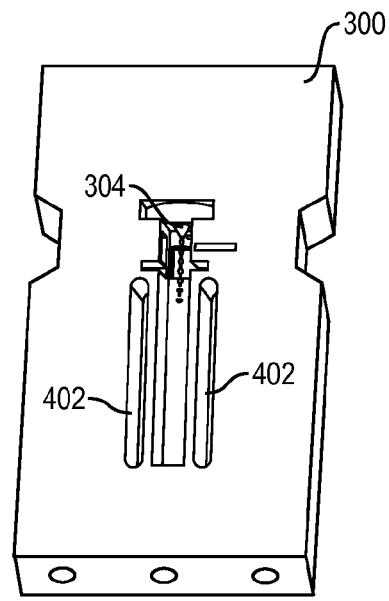
FIGS. 5A-E are perspective drawings of a flow cell for particle processing according to an illustrative embodiment of an aspect of the present invention, wherein the nozzle region, the particle interrogation region, the jet-forming region, the drop deflection region are at least partially cut away to allow the interior of a portion of the flow cell to be viewed.
Figure 5B:
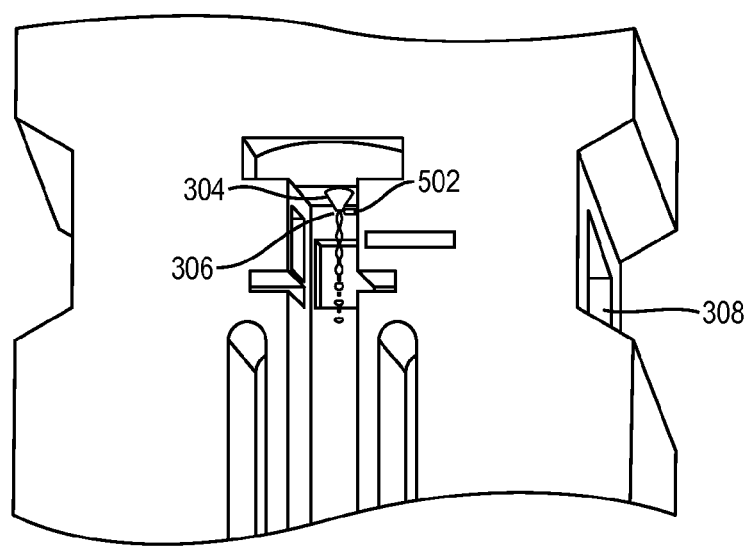
Figure 5C:
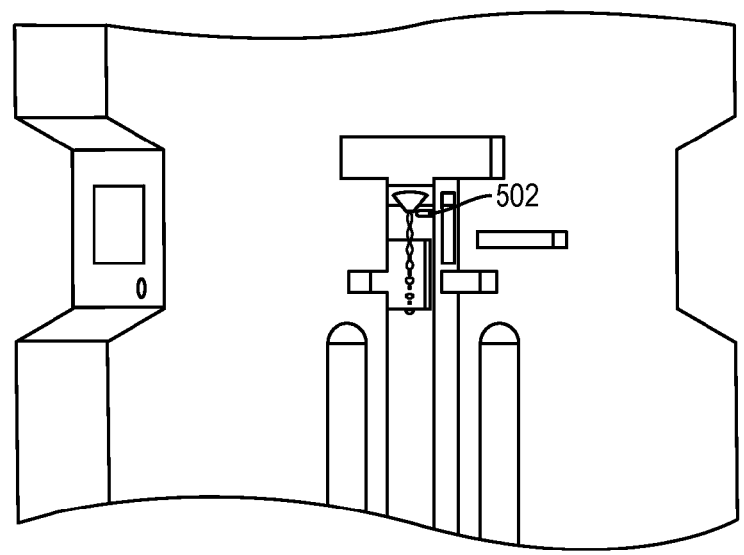
Figure 5D:
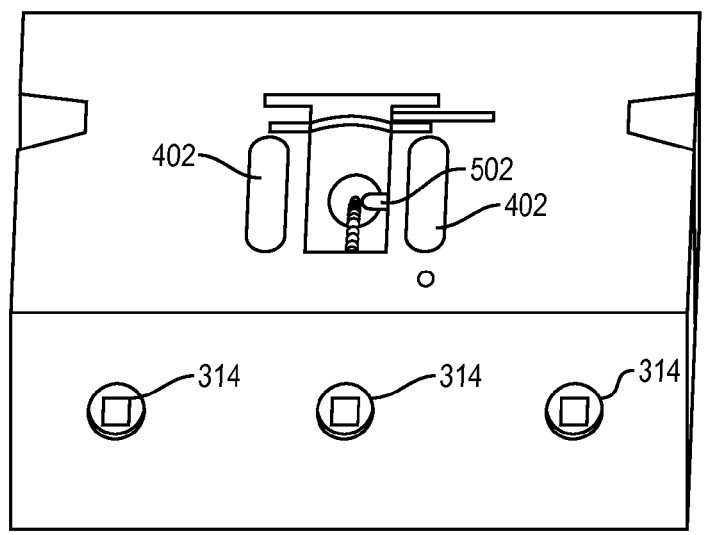
Figure 5E:
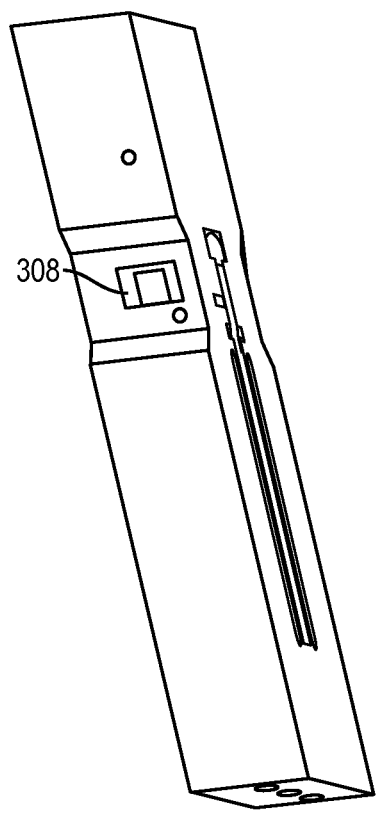

FIGS. 5A-5E are perspective drawings of an embodiment of flow cell 300 for cell sorting. FIG. 5A illustrates the flow cell removed from a holder and without charge plates. Charge plate access regions 402 are shown as recesses formed by flow cell 300 adjacent to the integrated nozzle region/sort chamber 304. FIG. 5B provides a close up view of flow cell 300, showing nozzle region 304, and optical transmission surface 308 disposed on the left side. FIGS. 5B and 5C depict an interrogation zone in close-up; wicking feature 502, discussed below, is also visible. In order to form a jet, and ultimately droplets of desired characteristics and dimensions, jet-forming element 306 may be provided of the same material or of a different material than that of the remainder of the flow cell. The jet-forming element 306 may be manufactured from any suitable material and may be appropriately coupled to the remainder of flow cell 300. Such materials may include, without limitation, polymers; ceramic; optical glass; or a natural or synthetic crystalline material such as sapphire. Coupling may occur during fabrication of the flow cell 300, or in a subsequent step. Alternatively, the orifice of the jet-forming element 306 may be formed through machining, drilling, laser etching, ablating, etc. FIG. 5D shows an embodiment of flow cell 300 from below. Exit ports 314 are shown, as are charge plate access regions 402 and jet-forming region 306. FIG. 5E is a lateral view of flow cell 300. An optical transmission surface 308 permits a lateral view of jet-forming region 306.

In one embodiment, a wicking feature is provided within the flow cell, (seen in FIGS. 5B-5D as element 502). The wicking feature may be disposed near a jet-forming element of the nozzle region in order to remove fluid (such as that produced by large droplet formation on the end of the tip due to surface tension or partial clogs of the orifice, rather than the desired fine stream of particles). When such a large droplet forms, it contacts the wicking feature, which acts to pull the drop away from the orifice and jet axis, thereby freeing the orifice to form a stream. The wicking feature may also be used to transport any such fluid formation to a collection vessel so as not to contaminate any desired fractions. Alternatively, a wicking function may be achieved by such means as a short burst of air, thermal or acoustic energy, which may act to remove fluid from the outlet of a jet-forming element in order to permit clean stable fluid flow and subsequent droplet formation.

Figure 6A:
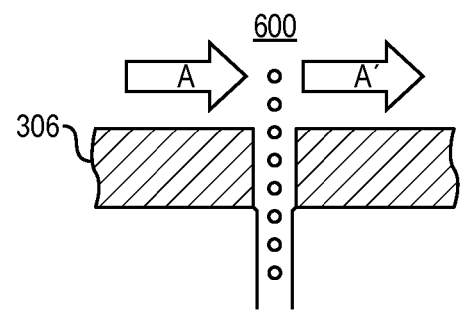
FIG. 6 is a close-up schematic view of a flow cell according to an embodiment of an aspect of the present invention showing three alternative placements of an excitation source relative to a jet-forming element, i.e., an excitation source is shown positioned relative to the flow cell unit at one of three points, i.e. before, during, or after the jet-forming element.
Figure 6B:
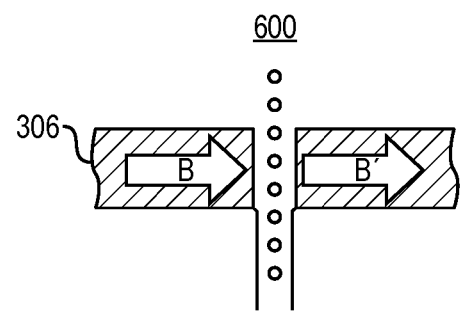
Figure 6C:
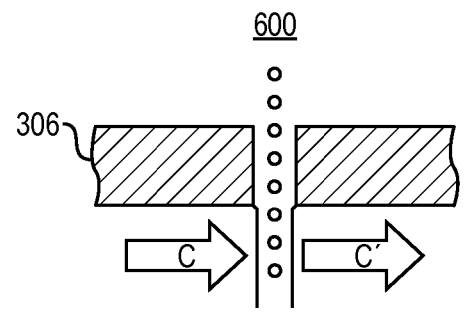

FIG. 6(a) shows excitation source A interrogating stream of particles 600 as they enter jet-forming element 306, which may be optically transmissive or may have optical transmission surfaces 308 disposed therein. FIG. 6(b) shows excitation source B interrogating the stream by passing through the jet-forming element 306, if optically transmissive, or through surface(s) 308. FIG. 6(c) shows excitation source C interrogating the stream as it exits the jet-forming element 306. Arrows A', B' and C' designate excitation sources exiting the flow cell and moving toward a detector.

Figure 7:
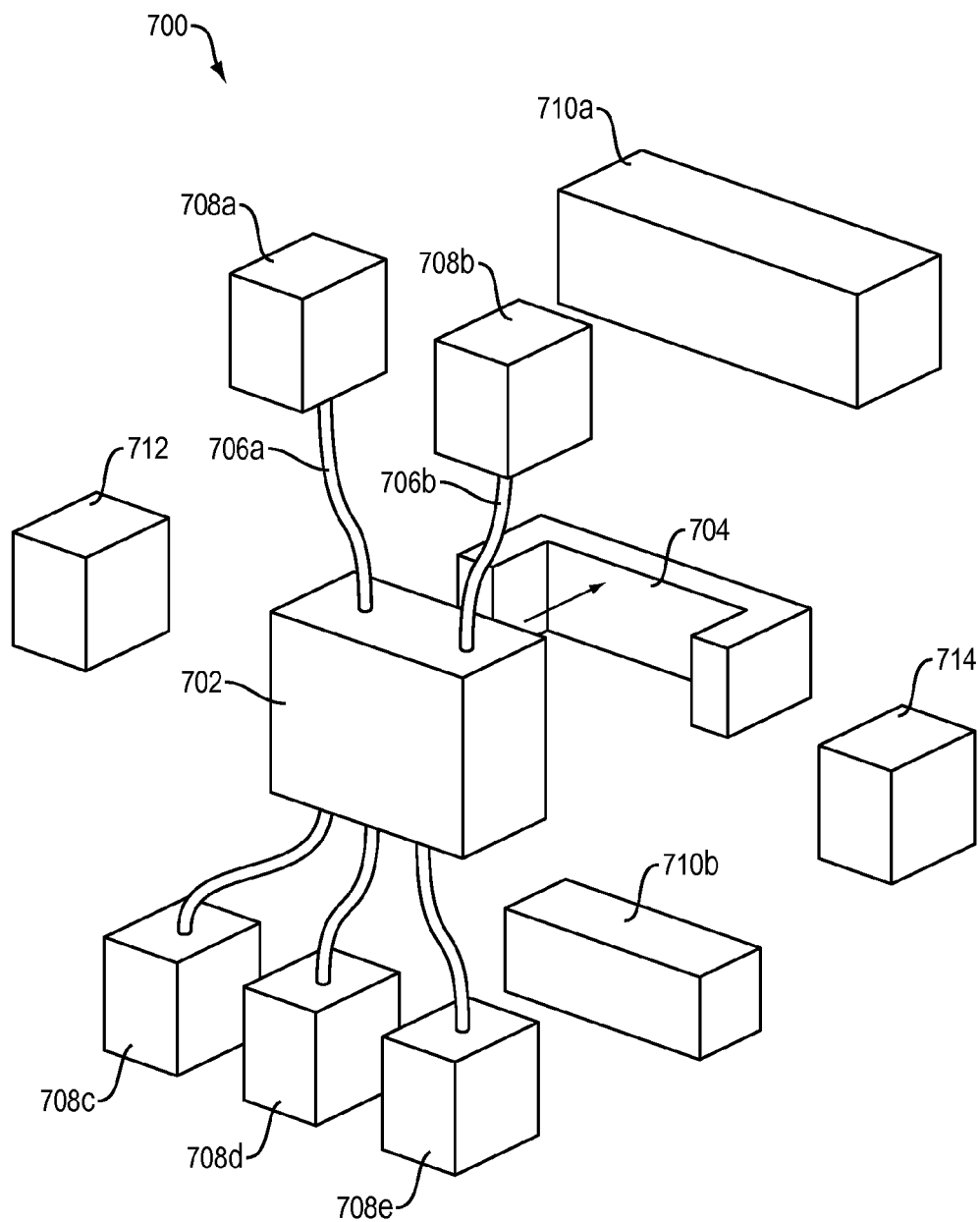
FIG. 7 schematically depicts a kit according to an illustrative embodiment of an aspect of the present invention.

FIG. 7 shows a kit 700 of the present invention, in exploded view. The kit includes flow cell 702 in communication with mount 704; flow paths 706a-e allow sheath and sample fluid to enter and exit as needed. Vessels 708a-e contain the fluids and may themselves be disposed in larger containers 710a and b, which serve as receptacles for the vessels but may also be used as interfaces for sensing and control functions. An excitation source (712) is in communication with the kit, as is at least one sensor (714). In exemplary fashion, the kit is assembled by attaching the flow cell to the mount and connecting the vessels/flow paths.

Figure 8:
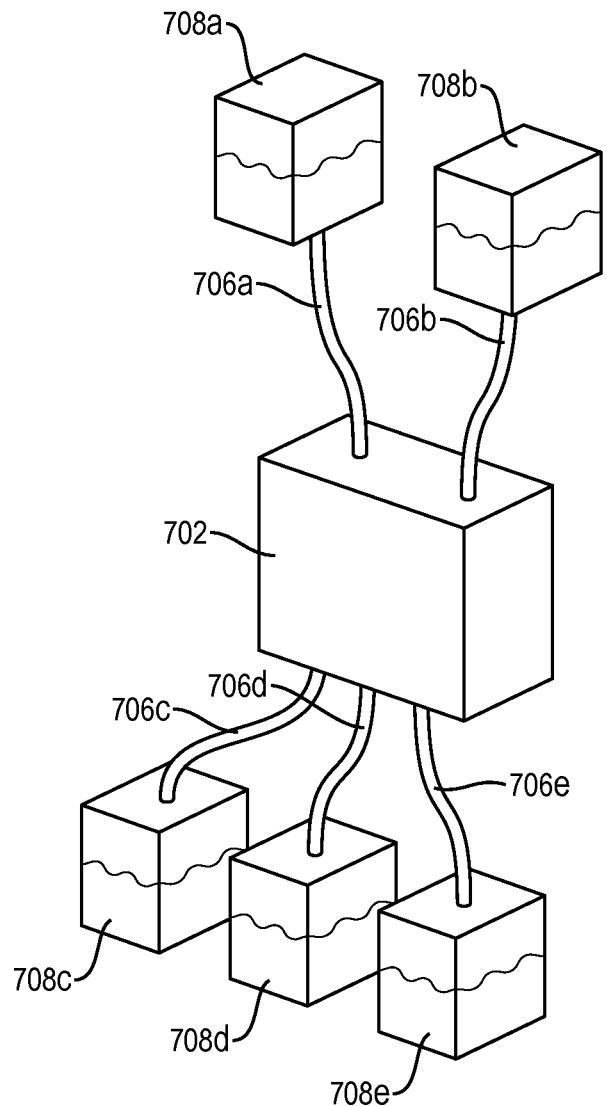
FIG. 8 schematically depicts a kit according to an illustrative embodiment of an aspect of the present invention.

FIG. 8 is another depiction of kit 700, showing flow cell 702 with attached flow paths 706a-e and vessels 708a-e. Fluid levels in vessels 708a and 708b indicate that particle sorting is about to commence.

Figure 9:
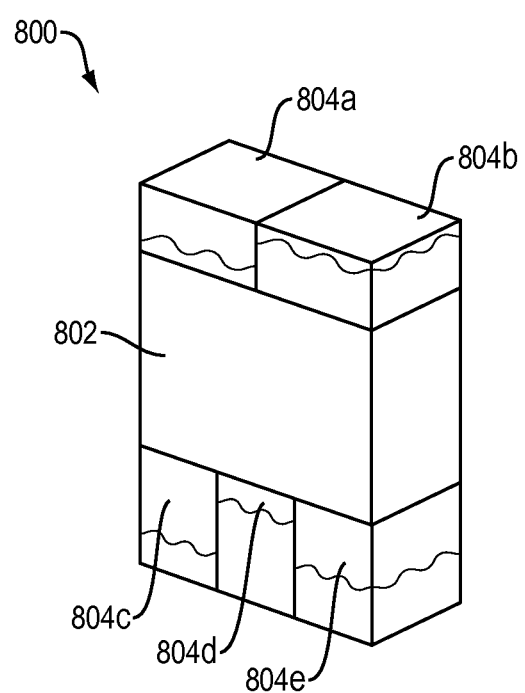
FIG. 9 schematically illustrates a flow cell according to an illustrative embodiment of an aspect of the present invention, wherein the flow cell is rigidly linked and integrated.

FIG. 9 shows a flow cell in a rigidly linked and integrated embodiment. Flow cell 800 is comprised of sort chamber 802 and vessels 804a-e, which provide entry and collection of sheath and sample fluid.

The figures illustrate a flow cell for performing a process on a sample, having many, and preferably all, fluid contact surfaces encapsulated within the flow cell. Thus, most, and preferably all, of the fluid contact surfaces are built into one enclosed and preferably operatively sealed object (i.e., the flow cell). The flow cell may be designed to perform any suitable process or multiple processes on a sample, including particle sorting.

According to certain embodiments, the flow cell includes a fully enclosed sort chamber. In general, the sort chamber may include one or more suitable devices for analyzing one or more predetermined characteristics of the particles and/or sorting particles based on the predetermined characteristic. Such suitable devices may include devices for focusing, aligning, accelerating, spacing, detecting, analyzing, switching, sorting or otherwise manipulating the fluid stream and/or the particles within the fluid stream.

Upstream of the sorting chamber the flow cell may include a sample vessel for storing particles in a fluid to be sorted and, optionally, a sheath fluid vessel storing a sheath fluid for facilitating a sorting process. The sample vessel and the optional sheath fluid vessel are in fluid communication with the sort chamber via sterile input ports. A means for applying pressure to the sample fluid within the sample vessel and the sheath fluid within the sheath fluid vessel applies pressure to induce or facilitate fluid flow through the flow cell. Channels within the sort chamber operatively and fluidically connect the input ports to the hydrodynamic focusing region.

Downstream of the sort chamber the flow cell includes collection vessels for collecting sorted particles. Channels and outlet ports within the sort chamber provide fluid communication between the droplet deflection region and the collection vessels. The flow cell including all the fluid contact surfaces may be removably inserted into a particle processing instrument. This particle processing instrument may be provided with sorting optics, electronics, control software and other subsystems. Due to the enclosed nature of the flow cell, the sample being processed never contacts the particle processing instrument.

During the manufacturing process, the flow cell may be sterilized after assembly all at once. The flow cell may then be shipped to the user in a sterile, ready to use form. Each flow cell (and therefore all fluid contact surfaces needed for a single processing run) can be given a barcode or other unique identification, making all of the parts that represent possible sources of product contamination fully traceable.

Use of the enclosed and sealed flow cell can enhance operator safety and product isolation. According to some embodiments, to use the flow cell to perform a particle processing operation, such as particle sorting, the operator can receive the flow cell sealed and sterile from the manufacturer. The operator may then take the flow cell to a biosafety hood, such as a sterile laminar flow hood, and perform a sterile operation (in the manner of conventional tissue culture for that type of sample) to load the sample and sheath vessels with the appropriate fluids. The flow cell is preferably sealed before and after this operation. The operator then couples the flow cell to the particle sorting instrument. The system sorts the cells or particles in the sample into one or more of the collection vessels in the flow cell. The operator removes the flow cell from the system. The flow cell may then be located back within the biosafety hood to remove the processed sample through an extraction port. The operator may then dispose of the used flow cell and unneeded fluids in a safe manner. In other words, no fluid waste needs to be removed from the flow cell in operation. Rather, fluid waste may be disposed of with the disposal of the flow cell, without requiring separate handling of the fluid waste.

In one embodiment, the flow cell is operated by being placed in the particle processing instrument which may perform one or more unit process operations on a sample that has been loaded into the flow cell. Examples of unit processes suitable for use with the flow cell include, but are not limited to, determining the number of particles in a sample, determining the type of particles in a sample, which may be a cytometry operation, sorting particles in the sample, collecting a subset of the particles in a sample, filtering the sample or a portion thereof to increase the concentration of particles therein, recycling a portion or a component of the sample, etc. Other unit processes may include washing, incubation, staining, mixing, testing, and/or changing the liquid or its chemical components in a sample, and the like.

The particle processing instrument that operates on the sample within the flow cell may use electrical, mechanical, pneumatic, optical, magnetic or other suitable actuation or sensing means known in the art to perform unit process operations on the sample in the flow cell. Examples of such actuation or sensing means include, but are not limited to, pneumatic means, fluid control means mechanical means, optical means, magnetic means, power means, and electrical means. To actuate or sense using a pneumatic means, a gas may be injected through a sterile filter to drive the sample from one vessel or chamber to another or from a vessel or chamber through a component such as a size filter and into a second chamber. Pneumatic means may also include gas injected through a sterile filter to clear blockages within channels or flow paths and/or to provide aerosol management. To actuate or sense using a fluid control means, a peristaltic pump head may be built into the flow cell so that an external rotor may fit into that head and by rotating it pump fluid from one vessel or chamber to another. Fluid control means may also include valves. To actuate or sense using an optical means, electromagnetic radiation may be directed to pass through a transmission surface in the flow cell in order to detect cells or particles that transiently block or scatter the radiation on its way to a photodetector. The transmission surface may be located within a particle interrogation region which may be provided as part of a microchannel, a focusing region, a nozzle region, an orifice region, a droplet detection region, etc. To actuate or sense using a magnetic means, a rotating magnet may be brought close to a vessel or chamber containing a conventional magnetic stir bar, causing that stir bar to rotate and stir or mix the fluid in that vessel or chamber. To actuate or sense using an electrical means, pressure, temperature or other sensors may be built into the flow cell. As another example of using an electrical means, a data storage means or a field programmable gate array, which may be part of a microcontroller or CPU, digital or analog, may be built into the flow cell thereby providing the flow cell with on-board data storage and/or intelligence function to support its use or standard operating procedures for handling the flow cell. Power for these devices may come from the particle processing instrument or be derived from batteries or electrical power storage means located within the flow cell.

The use of an attachable and detachable flow cell allows the particle processing instrument to be isolated from and external to the fluid contact surfaces. In this manner, the particle processing instrument can be used repeatedly, while the fluid contact surfaces within the flow cell may be disposable. Further, as has been described, the flow cell may be optimized for any given particle processing protocol by engineering into the flow cell specific, customized, unit processes.

To further enable any given particle processing protocol, the flow cell may contain one or more particle processing subsystems. These particle processing subsystems may be separately inserted into and/or removable from the flow cell or may be integrally provided with the flow cell. For example, the flow cell may include a vessel, chamber or receptacle for containing a mixing suspension, magnetic beads, stain, etc. or acting as a reservoir. As another example, a particle processing subsystem may include additional ports and/or fluid paths. Thus, an extraction port may be provided to access byproducts, if any. Optionally, one or more pneumatic ports in communication with the fluid paths may be provided to supply pressure to facilitate fluid flow through the flow cell.

The present invention has been described relative to multiple illustrative embodiments. Since certain changes may be made in the above constructions without departing from the scope of the invention, it is intended that all matter contained in the above description or shown in the accompanying drawings be interpreted as illustrative and not in a limiting sense. It is also to be understood that the following claims are to cover all generic and specific features of the invention described herein, and all statements of the scope of the invention which, as a matter of language, might be said to fall therebetween. A person of ordinary skill in the art would understand that variations to the embodiments may be made without departing from the scope of the following claims and are encompassed thereby.

We claim:

1. A flow cell for processing particles in a stream, comprising,
   an enclosed sort chamber including a first plurality of fluid contact surfaces and a second plurality of fluid contact surfaces, the first plurality of fluid contact surfaces forming a plurality of regions in fluid communication with one another and defining:
       a stream focusing region;
       an orifice located downstream of the focusing region;
       a particle interrogation region located downstream of the orifice; and
       a droplet deflection region;
   the second plurality of fluid contact surfaces defining a sample vessel provided upstream of the stream focusing region and in fluid communication with the stream focusing region,
   wherein the fluid contact surfaces of the sort chamber are integrally constructed,
   wherein the sort chamber includes at least one surface transmissible to electromagnetic radiation from an excitation source,
   wherein the flow cell is operatively sealed, and
   wherein the sample vessel is integrally constructed with the sort chamber.

2. The flow cell of claim 1, wherein a third plurality of the fluid contact surfaces define:
   a sheath vessel provided upstream of the stream focusing region and in fluid communication with the stream focusing region, wherein the sheath vessel is integrally constructed with the sort chamber.

3. The flow cell of claim 2, further comprising:
   a first flow control mechanism disposed between the sheath vessel and a first fluidic path and a second flow control mechanism disposed between the sample vessel and a second fluidic path.

4. The flow cell of claim 1, wherein the second plurality of fluid contact surfaces further define:
   one or more collection vessels provided downstream of the droplet deflection region and in fluid communication with the droplet deflection region, wherein the one or more collection vessels are integrally constructed with the sort chamber.

5. The flow cell of claim 1, wherein the sort chamber includes one or more optical transmission surfaces.

6. The flow cell of claim 1, wherein the second plurality of fluid contact surfaces further define one or more flow paths for recycling fluid from downstream of the droplet deflection region to upstream of the stream focusing region.

7. The flow cell of claim 1, wherein the sort chamber is configured to releasably accommodate a transducer in communication with the sort chamber to convert a fluid steam exiting the orifice into a series of droplets.

8. The flow cell of claim 1, wherein the orifice includes a converging region and a cylindrical region immediately downstream of the converging region.

9. The flow cell of claim 1, wherein the sort chamber is monolithically fabricated and the orifice is laser ablated.

10. The flow cell of claim 1, wherein the orifice is fabricated separately from the remainder of the sort chamber and integrally joined to the sort chamber after being separately fabricated.

11. The flow cell of claim 1, wherein the flow cell includes a flow control mechanism that is configured to operationally accommodate a peristaltic pump.

12. The flow cell of claim 1, wherein the stream focusing region includes a torsional hydrodynamic focusing region.

13. The flow cell of claim 1, wherein the orifice includes a cylindrical region having a diameter ranging from 50 microns to 100 microns and a length ranging from 75 microns to 250 microns.

14. The flow cell of claim 1, wherein the flow cell encloses all of the fluid contact surfaces for conducting a sort operation.

15. The flow cell of claim 1, wherein the sort chamber includes a surface acoustic wave generator configured to focus the stream.

* * * * *